US008700125B2

(12) United States Patent
Saranathan et al.

(10) Patent No.: US 8,700,125 B2
(45) Date of Patent: *Apr. 15, 2014

(54) METHOD AND APPARATUS FOR AUTOMATED TRACKING OF VESSEL MOVEMENT USING MR IMAGING

(71) Applicant: General Electric Company, Schenectady, NY (US)

(72) Inventors: Manojkumar Saranathan, Rochester, MN (US); Christopher Judson Hardy, Niskayuna, NY (US); Thomas Kwok-Fah Foo, Clifton Park, NY (US)

(73) Assignee: General Electric Company, Schenectady, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/746,983

(22) Filed: Jan. 22, 2013

(65) Prior Publication Data
US 2013/0131492 A1 May 23, 2013

Related U.S. Application Data

(63) Continuation of application No. 11/625,054, filed on Jan. 19, 2007, now Pat. No. 8,380,284, which is a continuation of application No. 09/728,071, filed on Nov. 30, 2000, now Pat. No. 7,209,777.

(51) Int. Cl.
*A61B 5/05* (2006.01)

(52) U.S. Cl.
USPC .............................. 600/410; 600/413; 382/278

(58) Field of Classification Search
USPC .............. 600/410, 413; 378/23; 382/243, 278
See application file for complete search history.

(56) References Cited

U.S. PATENT DOCUMENTS

| 5,485,086 A | 1/1996 | Meyer et al. |
| 5,759,152 A | 6/1998 | Felmlee et al. |
| 6,009,341 A | 12/1999 | Edelman |
| 6,044,290 A | 3/2000 | Vigen et al. |
| 6,057,680 A | 5/2000 | Foo et al. |
| 6,081,577 A | 6/2000 | Webber |
| 6,088,488 A | 7/2000 | Hardy et al. |
| 6,141,578 A | 10/2000 | Hardy |
| 6,198,959 B1 | 3/2001 | Wang |
| 6,408,201 B1 | 6/2002 | Foo et al. |
| 6,546,275 B2 | 4/2003 | Carroll |
| 6,556,856 B1 | 4/2003 | Mistretta et al. |
| 6,775,412 B1 | 8/2004 | Nister et al. |

OTHER PUBLICATIONS

Edelman et al., "Coronary Arteries: Breath-hold MR Angiography," Radiology, Dec. 1991, vol. 181, No. 3, pp. 641-643.

(Continued)

*Primary Examiner* — Unsu Jung
*Assistant Examiner* — Christopher Cook
(74) *Attorney, Agent, or Firm* — Ziolkowski Patent Solutions Group, SC

(57) ABSTRACT

A system and method is disclosed for tracking a moving object using magnetic resonance imaging. The technique includes acquiring a scout image scan having a number of image frames and extracting non-linear motion parameters from the number of image frames of the scout image scan. The technique includes prospectively shifting slice location using the non-linear motion parameters between slice locations while acquiring a series of MR images. The system and method are particularly useful in tracking coronary artery movement during the cardiac cycle to acquire the non-linear components of coronary artery movement during a diastolic portion of the R-R interval.

20 Claims, 5 Drawing Sheets

(56) References Cited

OTHER PUBLICATIONS

Manning et al., "A Preliminary Report Comparing Magnetic Resonance Coronary Angiography With Conventional Angiography," The New England Journal of Medicine, Mar. 25, 1993, vol. 328, No. 12, pp. 828-832.

Duerinckx et al., "Coronary MR Angiography During Peak-Systole: Work in Progress," Journal of Magnetic Resonance Imaging, 1997, vol. 7, pp. 979-986.

Foo et al., "Vessel Tracking: Prospective Adjustment of Section-selective MR Angiographic Locations for Improved Coronary Artery Visualization over the Cardiac Cycle," Radiology, Jan. 2000, vol. 214, No. 1, pp. 283-289.

Taylor et al., "Automated Monitoring of Diaphragm End-Expiratory Position for Real-Time Navigator Echo MR Coronary Angiography," Journal of Magnetic Resonance Imaging, Mar. 1999, vol. 9, No. 3, pp. 395-401.

Taylor et al., "Differences Between Normal Subjects and Patients With Coronary Artery Disease for Three Different MR Coronary Angiography Respiratory Suppression Techniques," Journal of Magnetic Resonance Imaging, Jun. 1999, vol. 9, No. 6, pp. 786-793.

Meyer et al., "Fast Spiral Coronary Artery Imaging," Magnetic Resonance in Medicine, 1992, vol. 28, pp. 202-213.

Hofman et al., "Quantification of In-Plane Motion of the Coronary Arteries During the Cardiac Cycle: Implications for Acquisition Window Duration for MR Flow Quantification," Journal of Magnetic Resonance Imaging, May/Jun. 1998, vol. 8, No. 3, pp. 568-576.

Wang et al., "Breath-Hold Three-dimensional Contrast-enhanced Coronary MR Angiography: Motion-matched k-Space Sampling for Reducing Cardiac Motion Effects," Radiology, May 2000, vol. 215, No. 2, pp. 600-607.

Sinha et al., "Estimation of the Left Ventricular Ejection Fraction Using a Novel Multiphase, Dark-Blood, Breath-Hold MR Imaging Technique," AJR, Jul. 1997, vol. 169, pp. 101-112.

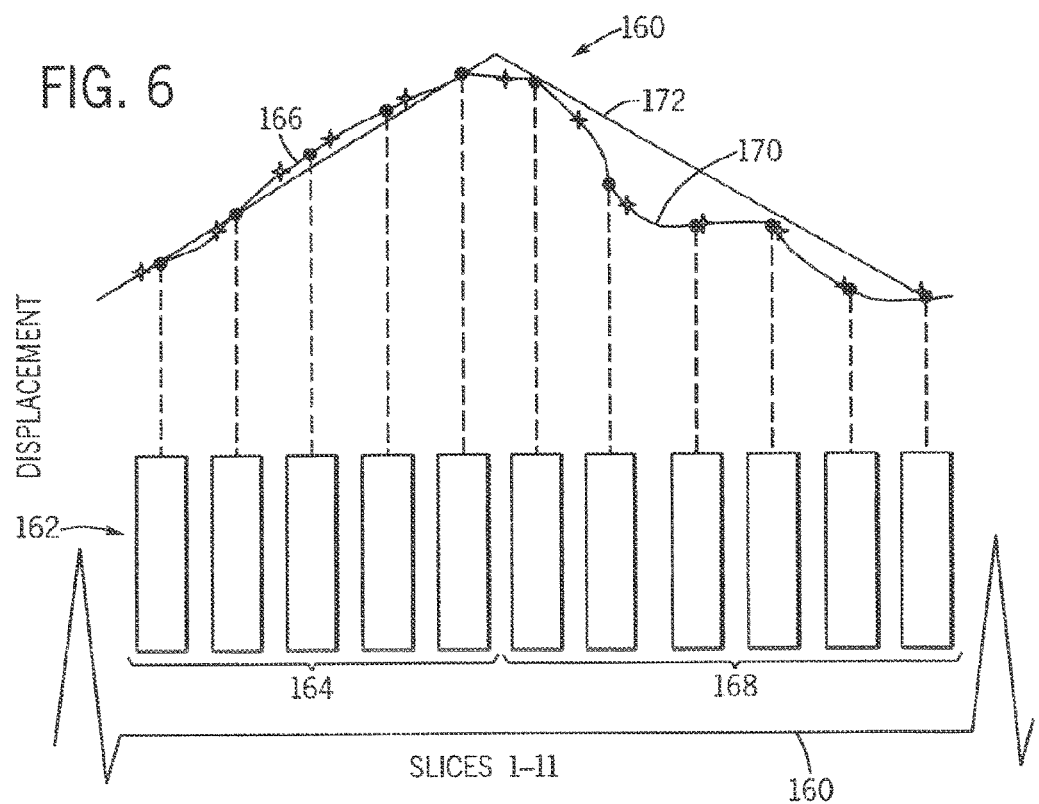

METHOD AND APPARATUS FOR AUTOMATED TRACKING OF VESSEL MOVEMENT USING MR IMAGING

CROSS REFERENCE TO RELATED APPLICATION

The present application is a continuation of and claims priority of U.S. Ser. No. 11/625,054, filed Jan. 19, 2007, which is a continuation of and claims priority of U.S. Ser. No. 09/728,071, filed on Nov. 30, 2000, now issued as U.S. Pat. No. 7,209,777, the disclosures of which are incorporated herein by reference.

BACKGROUND OF THE INVENTION

The present invention relates generally to an improved method for acquiring magnetic resonance images (MRI) of moving objects, and more particularly to, a method and apparatus to improve the efficiency of magnetic resonance coronary angiography (MRCA).

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients (Gx Gy and Gz) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

Moving objects are particularly difficult to image, especially if an imaging plane is set in space with the object moving in and out of the imaging plane. Such imaging is especially difficult when a second periodic motion is added thereto. For example, imaging of objects in a subject which is breathing causes a periodic motion of internal structures, which is also further complicated by the beating motion of the heart if the structure is near the heart.

Acquisition of images during an end-expiratory breath-hold is commonly employed to minimize respiratory artifacts, while electrocardiography (ECG) gating can effectively freeze cardiac motion. Breath-held, ECG-gated two-dimensional (2D) CMRA can be accomplished using several imaging strategies, the most common being a 2D fast gradient-echo sequence segmented k-space acquisition (fgre). Two strategies for 2D CMRA are acquisition of the same slice over the entire cardiac cycle (traditional "CINE") or acquisition of multiple slices with differing cardiac phases, typically acquired during mid-diastole. The prior art has successfully developed coronary artery imaging during the systolic phase, where a single image is acquired per acquisition. While such methods require that segments of the coronary artery be constrained within the plane of the prescribed slices, they do not make any implicit assumptions regarding the motion of the coronary arteries over the entire R-R interval. The visualization of the vessel-of-interest is therefore only ensured in a few frames.

Since there is substantial motion of the right coronary artery (RCA) and the left anterior descending (LAD) artery (in the order of 2 cm or more) during the cardiac cycle, the imaging efficiency (i.e., percentage of images containing a significant length of the vessel-of-interest) of these sequences is low. This implies that visualization of the vessel in its entirety generally requires several repeated breath-holds covering overlapping or contiguous slice locations, prolonging the scan times, which is generally not acceptable for patients with coronary artery disease.

The prior art proposed a method of tracking the motion of the coronary arteries prospectively across the cardiac cycle as a function of the delay from the cardiac trigger to improve the imaging efficiency. By adjusting the slice position as a function of cardiac phase, multiple images can be acquired in a single breath-hold, effectively tracking the vessel as a function of cardiac phase. This method reported an improved efficiency for the vessel tracking sequence compared to the multi-slice sequence. However, the prior art assumed a linear model for the motion of the vessel from its end-systolic to its end-diastolic position and back. While this linear model is often accurate in systole, during diastole, especially for the RCA, it is not. It has been found that the motion in diastole does not fit the linear model. As a consequence, the visualization efficiency in the diastolic phase, where the vessel moves the least, was less than optimal.

It would therefore be desirable to have a method and apparatus to improve the efficiency of acquiring MR images of a moving object by accurately, and automatically, tracking the moving object over a movement cycle. In particular, it is desirable to improve the efficiency of ECG-gated MRCA by accurate and automatic tracking of coronary vessel motion over the cardiac cycle.

SUMMARY OF THE INVENTION

The present invention relates to a system and method for imaging a moving object using magnetic resonance imaging (MRI) that utilizes non-linear object tracking to improve the efficiency of the imaging that solves the aforementioned problems.

The invention includes a technique that is a hybrid between multi-phase, single slice and single phase, multi-slice techniques. As applied to MR coronary angiography, the invention includes tracking coronary artery movement during a cardiac cycle as the coronary artery moves between two excursion positions in the R-R interval. The technique includes determining a function of the coronary artery movement having at least a non-linear component that represents movement during a diastolic portion of the R-R interval. Slice position acquisition is adjusted using the determined function and MR data is acquired during each such adjustment. The resulting MR images reconstructed have increased imaging efficiency using the MR data acquired.

In accordance with another aspect of the invention, a method of imaging a moving object using MRI includes acquiring a scout imaging scan having a number image frames, and extracting non-linear motion parameters from the number of image frames of the scout image scan. The method next includes acquiring a series of MR images while prospectively shifting a slice location using the non-linear motion parameters between slice locations. The method may take advantage of linear parameters as well as non-linear parameters to track the moving object.

Yet another aspect of the invention includes an MRI apparatus to track and image a moving object-of-interest that includes a magnetic resonance imaging system having an RF transceiver system and a plurality of gradient coils positioned about the bore of a magnet to impress a polarizing magnetic field. An RF switch is controlled by a pulse module to transmit RF signals to an RF coil assembly to acquire MR images. A computer is programmed to acquire a series of scout scans of the object-of-interest using a multi-phase, single slice acquisition pulse sequence as the object-of-interest moves from one position to another. A reference position in a scout scan is identified and the movement of the object-of-interest is tracked by isolating the reference position in each scout scan in the series of scout scans. A set of motion parameters are determined and stored that include non-linear parameters to accurately prospectively track movement of the object-of-interest.

In accordance with yet another aspect of the invention, a computer program is disclosed having a set of instructions which, when executed by a computer, cause the computer to track coronary artery movement during a cardiac cycle as the coronary artery moves between two positions. The computer is also caused to determine movement parameters of the coronary artery movement that has at least a non-linear component that represents movement during a diastolic portion of a R-R interval, and then stores the movement parameters in memory. Slice position acquisition is then adjusted using the stored movement parameters and image data is acquired during each such adjustment such that an image is reconstructed having increased imaging efficiency.

The imaging efficiency is defined as the percentage of the slices where more than 30 mm of the vessel is visualized. Since vessel tracking is preferably implemented on a spiral gradient-echo pulse sequence achieving sub-millimeter spatial resolution, as well as a higher signal-to-noise ratio (SNR), a significant improvement in the efficiency of the vessel tracking sequence was achieved. When using a cross-correlation algorithm for vessel tracking, imaging efficiency is increased even further. Additionally, a higher flip angle can be used to obtain improved image quality since the sequence repetition times are higher in the spiral sequence. The software implementing this technique can be integrated into the operator's console to achieve real-time prescription.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings:

FIG. 6 is a graph representing relative displacement versus slice acquisition in an R-R interval.

DETAILED DESCRIPTION OF THE PREFERRED EMBODIMENT

Figure 1:
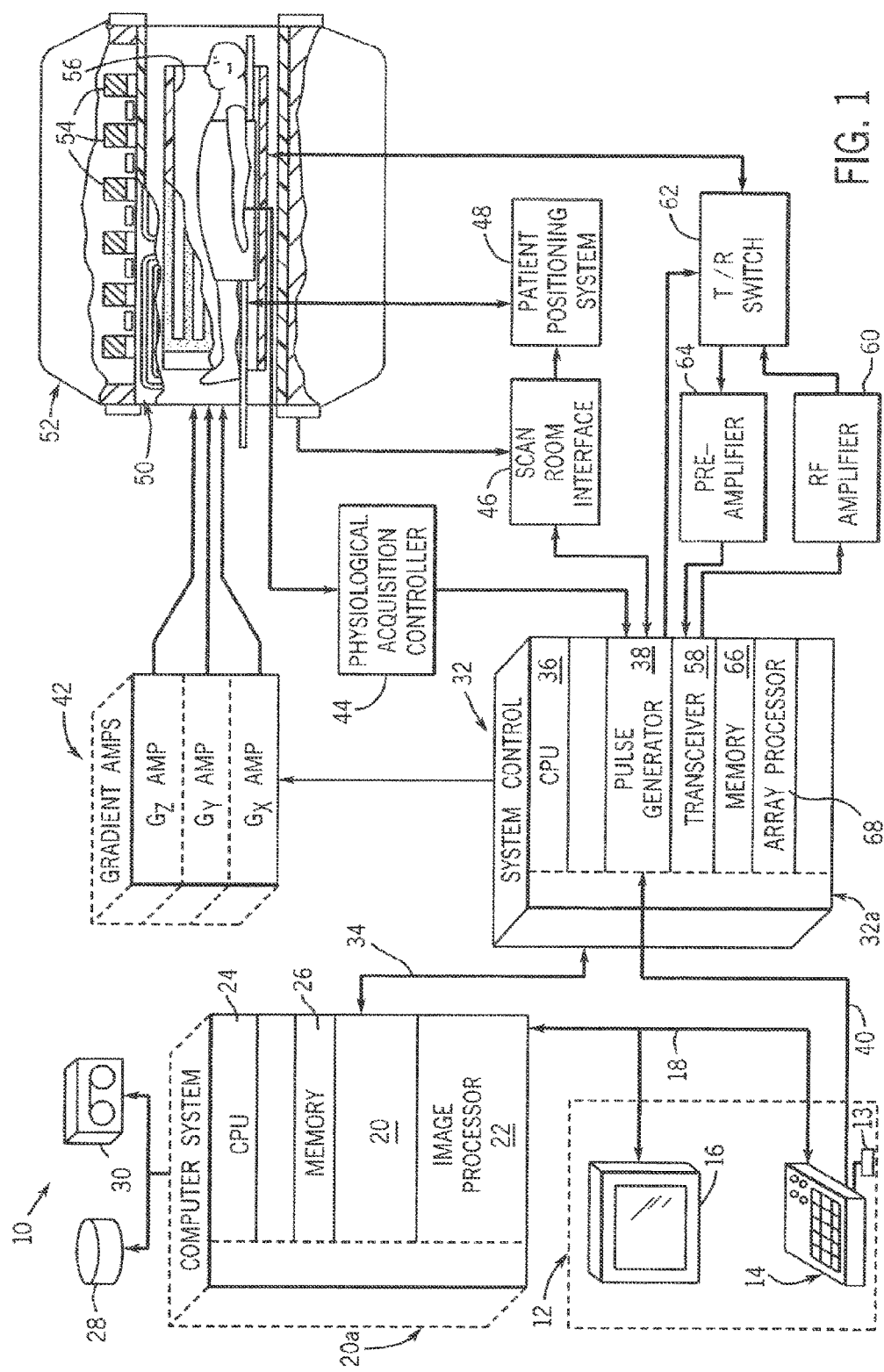
FIG. 1 is a schematic block diagram of an NMR imaging system for use with the present invention.

Referring to FIG. 1, the major components of a preferred MRI system 10 incorporating the present invention are shown. The operation of the system is controlled from an operator console 12 which includes a keyboard or other input device 13, a control panel 14, and a display 16. The console 12 communicates through a link 18 with a separate computer system 20 that enables an operator to control the production and display of images on the screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to a disk storage 28 and a tape drive 30 for storage of image data and programs, and it communicates with a separate system control 32 through a high speed serial link 34. The input device 13 can include a mouse, joystick, keyboard, track ball, touch screen, light wand, voice control, or similar device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator which indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 also receives patient data from a physiological acquisition controller 44 that receives signals from a number of different sensors connected to the patient, such as ECG signals from electrodes attached to the patient. And finally, the pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan.

The gradient waveforms produced by the pulse generator module 38 are applied to the gradient amplifier system 42 having $G_x$, $G_y$, and $G_z$ amplifiers. Each gradient amplifier excites a corresponding physical gradient coil in an assembly generally designated 50 to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 during the receive mode. The transmit/receive switch 62 also enables a separate RF coil (for example, a surface coil) to be used in either the transmit or receive mode.

The MR signals picked up by the RF coil 56 are digitized by the transceiver module 58 and transferred to a memory module 66 in the system control 32. When a scan is completed, an array of raw k-space data has been acquired in the memory module 66. As will be described in more detail below, this raw k-space data is rearranged into separate k-space data arrays for each image to be reconstructed, and each of these is input to an array processor 68 which operates to Fourier transform the data into an array of image data. This image data is conveyed through the serial link 34 to the computer system 20 where it is stored in the disk memory 28. In response to commands received from the operator console 12, this image data may be archived on the tape drive 30, or it may be further processed by the image processor 22 and conveyed to the operator console 12 and presented on the display 16.

The present invention includes a method and system suitable for use with the above-referenced MR system, or any similar or equivalent system for obtaining MR images, that when used with a fast-imaging technique, to acquire a set of scout frames, is used for automatically tracking and mapping object motion generally, and more specifically, to automatically map vessel trajectory to improve artery tracking in MR Angiography (MRA).

In accordance with the invention, in order to acquire MR images of a moving coronary artery in a specific scan plane, or plane of acquisition, it must first be prescribed (either graphically or by providing the computer with the location of at least two points of the acquisition or scan plane). The prescription of a scan or acquisition plane is customarily performed using a scout scan that is in a plane orthogonal to that of the acquisition or scan plane. From a multi-phase CINE acquisition at the same location and rotational orientation as the plane of the scout scan, the motion of the artery or any other vessel in the desired plane of acquisition or scan plane, during the cardiac cycle, can be observed. The maximum excursion or displacement of the vessel during the cardiac cycle, or R-R interval, can then be identified.

Figure 2:
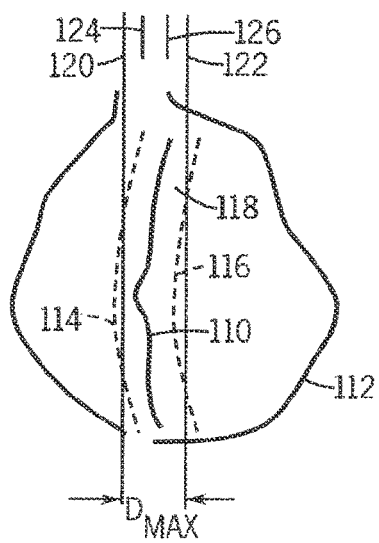
FIG. 2 is a diagram illustrating the maximum excursion positions of a coronary artery.

Referring to FIG. 2, there is shown a representation of such scout image, which depicts a coronary artery 110, such as a right coronary artery, within a heart 112. The artery 110 is located at one extreme position at the beginning of the cardiac cycle, i.e., the diastolic position of maximum excursion or end-diastolic position 114, progresses to the other extreme position, i.e. the systolic position of maximum excursion or end-systolic position 116, and returns to the starting location, i.e., end-diastolic position 114, at the conclusion of the cardiac cycle. The position of the coronary artery 110 is thus constrained to a region 118, lying between the two positions 114 and 116. Accordingly, it is unnecessary to prescribe imaging slice locations beyond the bounds determined by such maximum excursion positions 114 and 116, as observed from the CINE scout scan. Moreover, the maximum excursion of the artery 110, i.e., the displacement $D_{max}$ between maximum excursion positions 114 and 116, can be readily determined by simply measuring such displacement on the CINE scout image, by means of calipers or the like. The multi-phase scout acquisition will also provide information as to the obliquity of the coronary artery. The scout scan can be carried out, for example, in accordance with an MR imaging sequence which is conventionally available on MR imaging products of the General Electric Company, and which is referred to thereby as a CINE scout view sequence. As is known, a CINE sequence comprises a time resolved pulse sequence, i.e., a succession of views acquired at the same location but at different times. It will be readily apparent that a number of other MR techniques are available for use in determining the displacement between maximum excursion positions 114 and 116.

Once the region 118, which defines the possible locations of the coronary artery 110, and the maximum displacement $D_{max}$ have been determined, an algorithm can be derived to estimate the position of the coronary artery 110, or other vessel as a function of time or time delay following commencement of the cardiac cycle, or detection of the cardiac electrical R-wave trigger. MR data may be acquired throughout the cardiac cycle, with the slice excitation position adjusted as a function of the time delay of the RF pulse of the MR imaging sequence, likewise from the cardiac R-wave trigger. Thus, the MR scan or image acquisition plane, which corresponds to the position of a slice, can be adjusted or steered to track the location of the coronary artery 110, as the artery moves through the cardiac cycle.

In view of the effort to track the MR data acquisition with the motion of the artery 110, it is desirable to fit as many images as possible into the R-R interval. By using a segmented k-space approach, the maximum number of slice locations that will be acquired can be expressed as:

$$nslices_{max} = \frac{RR\_time}{vpsxTR + cs\_sattime} \qquad \text{Eqn. 1}$$

where $nslices_{max}$ is the maximum number of images per R-R interval, vps is the number of views or k-space lines acquired per segment (or per R-R interval), cs_sattime is the time needed to play out a fat suppression pulse, and TR is the sequence repetition time.

Referring further to FIG. 2, there is shown the data acquisition scan plane at a location 120, for a slice taken through end-diastolic position 114 at the beginning of the cardiac cycle. There is further shown the scan plane at a position 122, for a slice taken through the end-systolic position 116. The scan plane is at respective locations 124 and 126 for slices acquired at different locations within region 118. It will be readily apparent that a slice at a given location should be excited at a time during the cardiac cycle such that the coronary artery 110, or at least a substantial portion thereof, will also be at the given location at the time of excitation.

As is well known to those of skill in the art, the motion of a coronary artery is generally different during systole and diastole. The time for systole ($t_{systole}$) is calculated in milliseconds as follows:

$$t_{systole} = 546 - (2.1 \times HR) \qquad \text{Eqn. 2}$$

where HR is the heart rate in beats per min. From this expression, the time of diastole ($t_{diastole}$) in milliseconds can be calculated as follows:

$$t_{diastole} = \frac{60,000}{HR} - t_{systole}, \qquad \text{Eqn. 3}$$

The numerical parameters respectively used in Eqns. (2) and (3) are derived from teachings well known to those of skill in the art. An example of such a teaching is Bacharach S L, Bonow R O, Green M V, Comparison of fixed and variable temporal resolution methods for creating gated cardiac blood-pool image sequences, J. Nucl. Med. 1990; vol. 31: 38-42.

Figure 3:
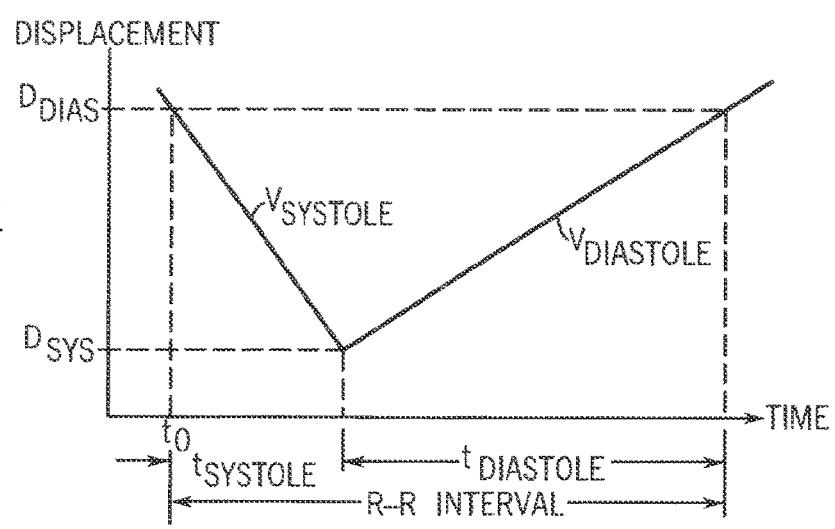
FIG. 3 is a prior art graph of artery displacement versus time for a linear model of artery motion over the cardiac cycle.

Referring to FIG. 3, there is shown a prior art time-displacement plot or curve, which represented displacement of artery 110 during the R-R interval, as the artery moves between end-diastolic position 114 and end-systolic position 116. Such prior art assumed a linear model for such motion, so that velocities $v_{systole}$ and $v_{diastole}$, the velocities during systolic and diastolic motion, respectively, had likewise been assumed to be constant. In FIG. 3, $D_{dias}$ indicates the position of coronary artery 110 identified in the scout scan as end-diastolic position 114, and $D_{sys}$ indicates the end-systolic position 116 identified thereby. Artery 110 is at $D_{dias}$ at the beginning of the cardiac cycle, and then moves in systole with a velocity $v_{systole}$ given by the following expression:

$$V_{systole} = \frac{(|D_{sys} - D_{dias}|)}{t_{systole}} \quad \text{Eqn. 4}$$

After the artery reaches end-systole position $D_{sys}$, it moves in diastole, in the opposite direction, at a velocity $v_{diastole}$ given by the following expression:

$$V_{diastole} = \frac{D_{dias} - D_{sys}}{t_{diastole}} \quad \text{Eqn. 5}$$

Figure 4:
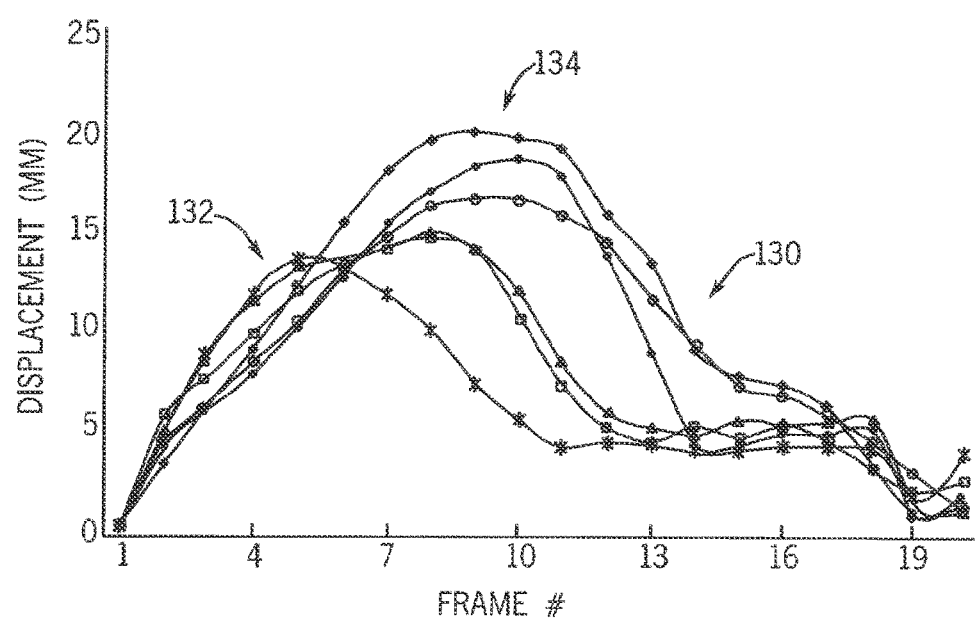
FIG. 4 is a graph showing displacement of the RCA as a function of position in the R-R interval for various subjects.

However, as shown in FIG. 4 the linear model of FIG. 3 is inaccurate during the diastolic phase generally shown with reference numeral 130. FIG. 4 shows the data points for eight subjects that depict the displacement of the right coronary artery (RCA) as a function of position in an R-R interval. As shown generally by reference character 132, the systolic displacement can generally be estimated as a linear function as compared to the more non-linear behavior of the diastolic displacement 130. The peak displacements 134 corresponds with end-systole.

In accordance with the present invention, a cross-correlation algorithm is used to track the motion of the coronary arteries and the results are used to prospectively adjust slice position selection and acquisition. A region-of-interest (ROI) that includes the RCA is identified in the systolic frame and used as a convolution kernel to compute the cross-correlation data for the entire set. The central intensity maximum, or peak, in the cross-correlation image essentially describes the motion of the RCA. The position of the central peak and its displacement from the systolic frame position (i.e., the first frame position) is then automatically computed for each of the desired frames. In a preferred embodiment, the data is then saved to a file and can be used by the desired pulse sequence to prospectively shift the slice location to maximize the imaging efficiency. These computations and the file output take about 1-2 minutes, including image transfer times, resulting in near real-time performance. Moreover, errors due to breath-holding inconsistencies can be ignored since the displacements are all relative to the systolic position.

In the preferred embodiment, a method and apparatus is disclosed for more accurate, and automated tracking of coronary arteries. The process includes using a multi-phase, single slice scout scan to depict the vessel of interest in cross-section over a given cardiac cycle. The process then uses image processing techniques to extract the motion of the coronary arteries. The information obtained with regard to coronary artery motion is then used to prospectively adjust the acquisition of slice positions to improve tracking accuracy. In a preferred embodiment, the right and left coronary arteries are localized using combinations of sagittal, coronal, and oblique breath-held scout frames obtained using breath-held 2D multi-slice fgre sequences. A prerequisite breath-held CINE scan is first acquired to depict the motion of the cross-section of the proximal and distal coronary artery across the cardiac cycle. It is noted that for the RCA, only the proximal RCA (cross-section) is used for the analysis since it provides a much more discernable image than the typically smaller distal RCA over the entire R-R interval. All breath-held images are acquired at end-expiration to improve reproducibility in achieving comparable diaphragm positions from one scan to the next.

Figure 5:
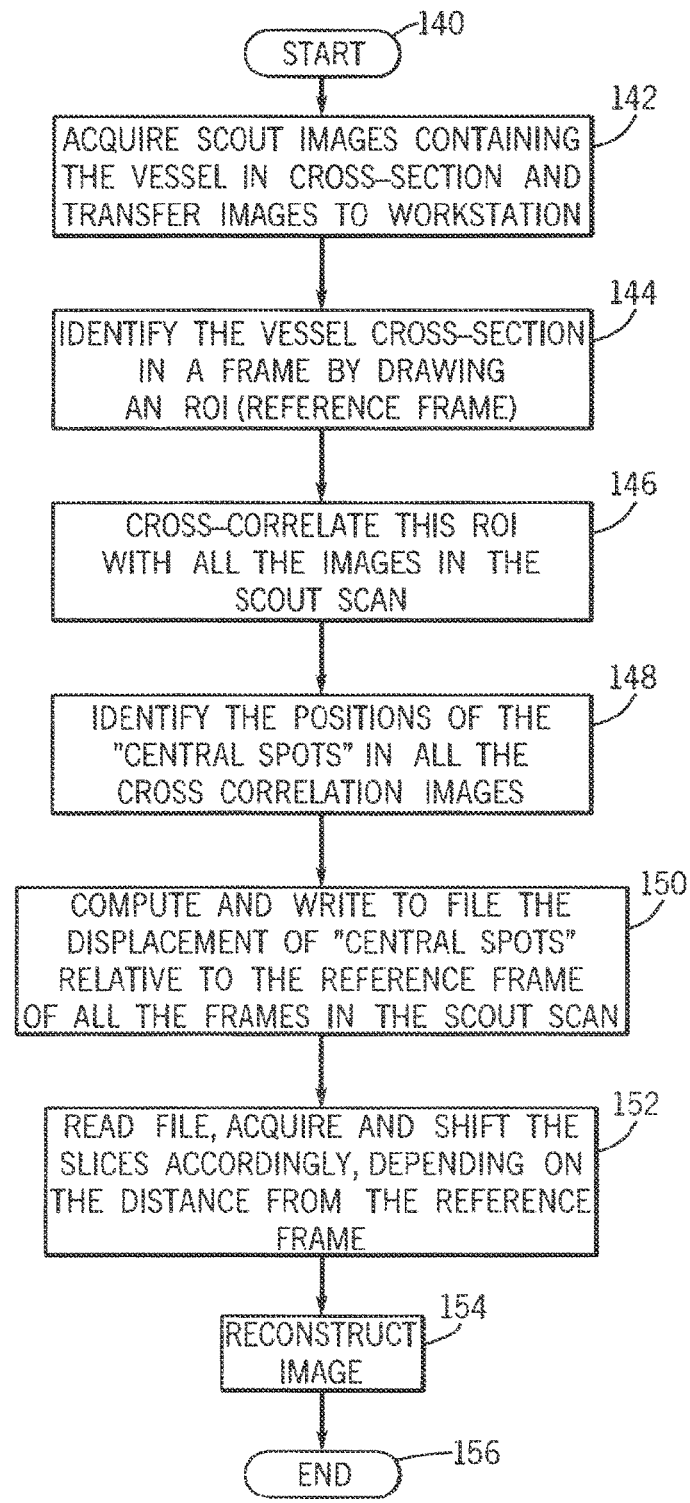
FIG. 5 is a flow chart of a technique employed in the present invention.

FIG. 5 is a flow chart showing the steps of the present invention. Upon startup 140, the motion of the vessel is then analyzed using the CINE images of an imaging plane containing the proximal and distal portions in cross-section, and then transferring the images to a workstation for post-processing 142. Preferably, this processing is done using IDL software (Research Systems, Inc. Boulder, Colo.) on an Ultra-Sparc 2 Workstation (Sun Microsystems, Mountain View, Calif.) networked to the scanner for transfer of images. The user then delineates a region-of-interest (ROI) containing the RCA in one frame 144. Typically, this reference frame is chosen as the one in which the RCA is most discernible. A cross-correlation algorithm is then applied between the ROI and all the frames to yield a set of correlation maps 146. After the cross-correlation algorithm is applied, the displacement of the central peaks relative to the reference frame for each of the frames in the scout scan is then written to a file 150. Accordingly, the positional information of the RCA in the different frames is preferably used to compute the displacements relative to the systolic position across the cardiac cycle.

During testing, it was found that the entire process can be completed in less than a minute, including transfer of the CINE images and the correlation analysis. This displacement information is then used to acquire a series of MR images while prospectively shifting a slice location using these non-linear motion parameters between slice acquisitions. In acquiring the MR data, the displacement information is read from the file and used to acquire and shift the slices depending on the distance from the reference frame 152. Additionally, the slices may be reoriented or rotated during the acquisition process to acquire more desirable images. Preferably, the acquisition of MR data is accomplished using a 2D spiral gradient echo pulse sequence with repetition times and flip angles of approximately 100 ms/40°-60° for the vessel tracking sequence and 900-1000 ms/70°-75° flip angle for the multi-slice sequence. Between 12 and 16 interleaves with 2048-4096 points per interleave were acquired at a receiver bandwidth of ±125 kilohertz. The average breath-holding time for each multi-slice or vessel tracked acquisition was about 15 seconds. All acquisitions were acquired during end-expiration breath-holds. After reconstructing the images 154, the process is complete at 156.

Referring now to FIG. 6, a graphical representation of slice acquisition across an R-R interval 160 is shown. In this particular case, an exemplary eleven slices 162 are acquired over the cardiac cycle 160, but each phase is acquired at a different location depending on the position within the R-R interval 160. The first five slices 164 are acquired during a systolic portion 166 of the R-R interval, and the final six slices 168 are acquired during the diastolic portion 170 of the R-R interval 160. The systolic and diastolic curves 166, 170 show the displacement relative to the first frame. FIG. 6 accentuates the deviation of the actual vessel trajectory 166, 170 from the linear model 172, as was described with reference to FIG. 3, particularly, in diastole. The star data points indicate displacements stored in the file, and the circle data points indicate displacements at slice locations as computed by interpolation of the data from the file.

There are many different cross-correlation algorithms that may be used with the present invention. However, one preferred cross-correlation algorithm will be briefly described. In this algorithm, once a reference image R is acquired and a first region-of-interest ROI is identified in the reference image R, image ROI can be cross-correlated with each of the other images from a series of images to result in a series of cross-correlation images. The cross-correlation algorithm includes first inverse Fourier transforming the reference image R within the ROI into a k-space image, flipping the k-space image with respect to its X coordinates, and then flipping the k-space image with respect to its Y coordinates to result in a kernel set K. A mask M is also created having zeros outside of the ROI and one's inside of the ROI. The mask M is then inverse Fourier transformed into a k-space image and the k-space image of the mask M is flipped with respect to its X coordinates and then flipped with respect to its Y coordinates to result in a weighting set W. The kernel set K and the weighting set W are then each multiplied by a raw data image D to result in a product K, and a product W, respectively. A 2D Fourier transform is then performed on product K and product W to result in amplitude and phase information $(A_2, \phi_2)$, and $(A_1, \phi_1)$, respectively. The magnitudes $\|I_2\|, \|I_1\|$ are determined from the amplitude and phase information $(A_2, \phi_2)$, and $(A_1, \phi_1)$. The cross-correlation image $I_C$ is then determined from $$I_C = \frac{\|I_2\|}{\|I_1\|}.$$

Since at each location, $I_2$ is divided by $I_1$ to result in $I_c$ being the intensity of the correlation at that location, a two-dimensional correlation map is developed. One skilled in the art will readily recognize such cross-correlation with the initial position in a region-of-interest with a position in a region-of-interest for subsequent images can be used to extract the non-linear motion parameters. This is just one example of a cross-correlation algorithm, many others are also applicable.

Accordingly, the present invention includes a method of imaging a moving object using MRI that includes acquiring a scout image scan having a number of image frames, and extracting non-linear motion parameters from the number of image frames from the scout image scan. The method next includes acquiring a series of MR images while prospectively shifting a slice location using the non-linear motion parameters between slice acquisitions. The motion parameters can include linear parameters and non-linear parameters, depending upon the object to be imaged. For example, in coronary artery imaging, the systolic portion of the R-R interval can be estimated using linear parameters, while the diastolic portion can be estimated using non-linear parameters. The method can also include the steps of selecting a region-of-interest encompassing a coronary artery, recording a reference position in the region-of-interest, and then cross-correlating the reference position with a similar position in the region-of-interest for subsequent image frames to extract the non-linear motion parameters.

One of the disadvantages of using a vessel tracked sequence is in-plane saturation. For example, if the coronary artery is being tracked, the same slice is repeatedly excited, necessitating the use of smaller flip angles. It is anticipated that the use of a spiral pulse sequence with the technique of the present invention will benefit from the use of contrast agents to enable the use of higher flip angles.

Further, the automatic mapping of the vessel trajectories can prove valuable in reordering k-space for minimizing motion artifacts. Data corresponding to higher k-space values are less sensitive to motion compared to those from lower, or central k-space. By suitably reordering k-space data, more data can be acquired in an R-R interval, or motion can be minimized in the acquired data by using such information. This can then help reduce scan times by improving scan efficiency.

The present invention also includes a method of coronary MR angiography imaging that includes tracking coronary artery movement during a cardiac cycle as the coronary artery moves between two excursion positions, and determining a function of the coronary artery movement, where the function includes at least a non-linear component that represents movement during a diastolic portion of an R-R interval. The method includes adjusting slice position acquisition using the determined function, and acquiring MR data during each such adjustment. MR images can then be reconstructed having increased imaging efficiency.

Preferably, the MR data is acquired in a single breath-held R-R interval. The step of tracking coronary artery movement is accomplished by acquiring a set of scout frames and developing a non-linear motion function based on the relative position of the coronary artery in each scout frame. A reference kernel derived from an ROI in one scout frame is cross-correlated with the other scout frames to develop the non-linear motion function. The scout frames are preferably acquired using a CINE pulse sequence to track coronary artery movement. A 2D spiral pulse sequence is used to acquire the MR data based on the displacement determined from the scout frames.

The invention also includes an MRI apparatus to track and image a moving object-of-interest that includes an MRI system, such as that described with reference to FIG. 1, and a computer, also as described with reference to FIG. 1, that is programmed to acquire a series of scout scans of the object-of-interest using a multi-phase, single slice acquisition pulse sequence as the object-of-interest moves from one position to another. The computer is also programmed to identify a reference position in a scout scan, and track movement of the object-of-interest by isolating the reference position in each scout scan. A set of motion parameters are determined and stored that are then used to track movement of the object-of-interest that has non-linear motion characteristics. The motion parameters are then used to acquire MR data at differing slice locations, each slice location offset from a previous slice location based on the displacement of the scout scans.

Accordingly, the present invention also includes a computer program comprising instructions which, when executed by a computer, cause the computer to track coronary artery movement during a cardiac cycle as the coronary artery moves between two positions, and determine movement parameters of coronary artery movement. These movement parameters have at least a non-linear component that represents movement during a diastolic portion of an R-R interval. The computer program also causes the computer to adjust slice position acquisition using the stored movement parameters and acquire image data during each such adjustment. An image is then reconstructed having increased imaging efficiency using the image data acquired.

It is noted that this technique can be used for other purposes, such as the tracking of motion in valve planes to help characterize valvular disease. Such tracking can be conducted in a similar manner as that described with reference to coronary artery tracking.

It is noted that all imaging tests were performed on a cardiovascular 1.5 T MR scanner (CVi, General Electric Medical Systems, Waukesha, Wis.) equipped with high performance gradients (40 mT/m, 150 T/m/s) using a dedicated four-channel phased array coil. Further, while previous vessel tracking techniques used a segmented k-space fast gradient recalled echo sequence (fgre), the present invention preferably employs a 2D spiral pulse sequence. Spiral sequences have been shown to yield higher SNR images of the coronary artery due to the longer sequence repetition times and the higher flip angles. Furthermore, the more efficient coverage of k-space per RF excitation pulse, yields a higher spatial resolution for the same scan time. Accordingly, in-plane spatial resolution of approximately 0.8 mm is achievable using this sequence.

While not shown, a persistence can be added at end-systole, to account for the fact that the heart stays in the end-systolic position for 30-70 milliseconds.

The present invention has been described in terms of the preferred embodiment, and it is recognized that equivalents, alternatives, and modifications, aside from those expressly stated, are possible and within the scope of the appending claims.

What is claimed is:

1. A magnetic resonance (MR) imaging apparatus comprising:
 a plurality of gradient coils positioned about a bore of a magnet;
 an RF transceiver system and an RF switch controlled by a pulse module to transmit RF pulses to an RF coil assembly and receive MR signals therefrom; and
 a controller programmed to:
  cause acquisition of a series of scout images;
  determine a non-linear motion of an anatomy of interest among the series of scout images; and
  adjust a position of an acquisition slice during MR image acquisition based on the non-linear motion of the anatomy of interest.

2. The MR apparatus of claim 1 wherein the controller is further programmed to define a region of interest (ROI) within a reference image of the series of scout images, the ROI containing the anatomy of interest.

3. The MR apparatus of claim 2 wherein the controller is further programmed to determine the non-linear motion of the anatomy of interest by cross-correlating positions of the ROI between the reference image and additional images of the series of scout images.

4. The MR apparatus of claim 3 wherein the controller is further programmed to define the region of interest and cross-correlate positions thereof for all images of the series of scout images.

5. The MR apparatus of claim 3 wherein the controller is further programmed to cross-correlate the positions of the ROI by using the reference image as a convolution kernel and convolving the more than three of the series of scout images with the convolution kernel.

6. The MR apparatus of claim 5 wherein the controller is further programmed to identify a number of displacement values of central convolution peaks from cross-correlating the positions of the ROI.

7. The MR apparatus of claim 6 wherein the controller is further programmed to determine the motion of the anatomy of interest from the displacement values and adjust the position of the acquisition slice by modifying a slice selection gradient of the MR image acquisition according to the displacement values.

8. A method of coronary MR imaging comprising:
 identifying a region of interest (ROI) in a reference scout image generated by a magnetic resonance (MR) apparatus; and
 in a computer operational with the MR apparatus:
  (A) cross-correlating positions of the ROI between the reference scout image and each of a series of scout images acquired by the MR apparatus during an R-R interval;
  (B) determining a plurality of cross-correlation maps from the cross-correlated positions of the ROI, wherein the plurality of cross-correlation maps define a non-linear motion of the anatomy of interest; and
  (C) applying the cross-correlation maps to define a plurality of acquisition slices during MR imaging of the region of interest.

9. The method of claim 8 further comprising:
 acquiring a plurality of CINE scout images from a CINE scout scan; and
 selecting the reference image as an image of the plurality of CINE scout images in which the ROI is most discernible.

10. The method of claim 8 wherein cross-correlating positions of the ROI includes Fourier transforming the reference scout image and determining a kernel set therefrom.

11. The method of claim 10 wherein cross-correlating positions of the ROI further includes creating a mask of the ROI and determining a weighting set therefrom.

12. The method of claim 11 wherein cross-correlating positions of the ROI further includes multiplying the kernel set and the weighting set by a raw data image to result in a kernel product and a weighting product, and calculating a cross-correlation image from a ratio of the magnitudes of the kernel product and the weighting product.

13. The method of claim 8 wherein the plurality of cross-correlation maps define a non-linear motion of the anatomy of interest during one phase of motion of the anatomy of interest.

14. The method of claim 8 further comprising tracking motion of a coronary artery by positioning the number of acquisition slices to maintain the coronary artery in a field of view of each acquisition slice.

15. A non-transitory computer readable storage medium having stored thereon a set of instructions which, when executed by a computer, cause the computer to:
 identify a region of interest (ROI) in a series of scout images;
 extract a plurality of motion parameters from the series of scout images, wherein the plurality of motion parameters define non-linear motion of the ROI; and
 adjust an acquisition slice location during MR imaging using the plurality of motion parameters.

16. The computer readable storage medium of claim 15 wherein the set of instructions further causes the computer to:
 cross-correlate a position of the ROI in one image of the series of scout images with positions of the ROI in other images of the series of scout images; and
 generate a cross-correlation map from the cross-correlated positions of the ROI.

17. The computer readable storage medium of claim 16 wherein the set of instructions further causes the computer to cross-correlate the positions of the ROI using the one image of the series of scout images as a convolution kernel and convolving the other images of the series of scout images with the convolution kernel.

18. The computer readable storage medium of claim 15 wherein the set of instructions further causes the computer to extract the plurality of motion parameters during one phase of motion of an anatomy of interest.

19. The computer readable storage medium of claim 15 wherein the set of instructions further causes the computer to identify a displacement of a central intensity maximum of the ROI in the series of scout images.

20. The computer readable storage medium of claim 15 wherein the set of instructions further causes the computer to adjust the acquisition slice location by modifying a slice selection gradient.

* * * * *